United States Patent
Jorgensen

(10) Patent No.: US 9,307,872 B2
(45) Date of Patent: Apr. 12, 2016

(54) FOOT HYGIENE DEVICE

(71) Applicant: Nancy Ruth Jorgensen, Fort Bragg, CA (US)

(72) Inventor: Nancy Ruth Jorgensen, Fort Bragg, CA (US)

(73) Assignee: Nancy Ruth Jorgensen, Fort Bragg, CA (US)

( * ) Notice: Subject to any disclaimer, the term of this patent is extended or adjusted under 35 U.S.C. 154(b) by 79 days.

(21) Appl. No.: 13/850,433

(22) Filed: Mar. 26, 2013

(65) Prior Publication Data

US 2014/0290086 A1 Oct. 2, 2014

(51) Int. Cl.
*A61M 35/00* (2006.01)
*A47K 7/02* (2006.01)

(52) U.S. Cl.
CPC ............... *A47K 7/026* (2013.01); *A61M 35/003* (2013.01)

(58) Field of Classification Search
CPC ........ A61H 35/06; A61M 35/00; A47K 7/026
USPC ........ 604/293, 289, 1; 601/84, 135, 136, 137; 15/104.92, 114, 118, 144.1, 244.1, 15/244.3, 104.94, 209.1, 233, 231; 132/74.5
See application file for complete search history.

(56) References Cited

U.S. PATENT DOCUMENTS

| | | | | | |
|---|---|---|---|---|---|
| 3,531,814 | A | * | 10/1970 | Safalow | 15/114 |
| 4,532,668 | A | * | 8/1985 | Slonicki | 15/104.92 |
| 4,961,733 | A | * | 10/1990 | Joseph | A47K 7/026 15/114 |
| 5,444,888 | A | * | 8/1995 | Withey | A47K 7/026 15/114 |
| 5,671,497 | A | * | 9/1997 | Abdo | 15/144.1 |
| 5,960,509 | A | * | 10/1999 | Wu | 15/244.2 |
| 6,340,026 | B1 | * | 1/2002 | Shapiro | A45D 29/00 132/73 |
| 6,370,723 | B1 | * | 4/2002 | Chang | 15/110 |
| 7,174,595 | B2 | * | 2/2007 | Chen | 15/110 |
| 7,178,192 | B2 | * | 2/2007 | Huang | 15/209.1 |
| 7,213,292 | B1 | * | 5/2007 | Tucker | 15/144.1 |
| 2005/0059920 | A1 | * | 3/2005 | Baril | 604/1 |
| 2006/0130258 | A1 | * | 6/2006 | Ge | A47K 7/026 15/210.1 |
| 2011/0067195 | A1 | * | 3/2011 | Oehler | A47K 7/026 15/210.1 |

* cited by examiner

*Primary Examiner* — Nina Bhat

(57) ABSTRACT

A device for foot hygiene comprising a holder, an arch and a fabric strip attached across the arc of the arch is provided.

9 Claims, 1 Drawing Sheet

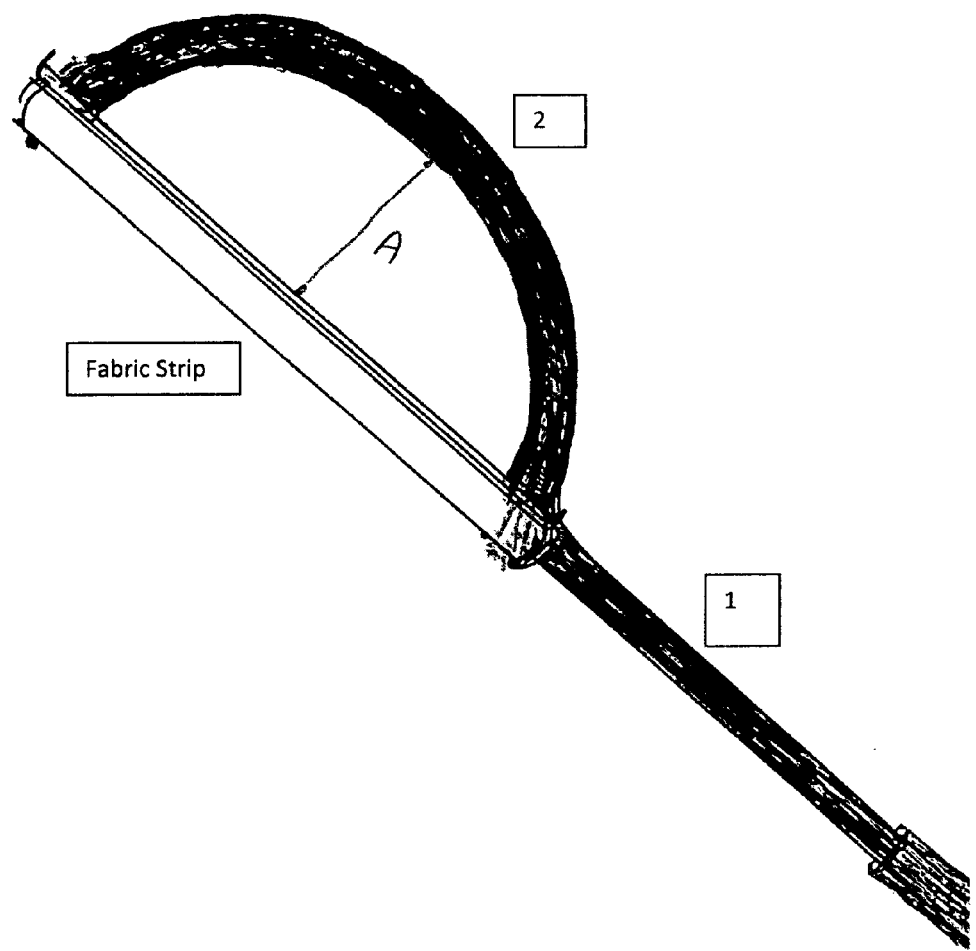

FOOT HYGIENE DEVICE

DESCRIPTION OF THE INVENTION

A device for personal hygiene of the feet is described. This device is particularly useful for the mobility impaired, those who have difficulty bending at the waist or are otherwise precluded from reaching the foot. The device comprises an arched holder that constrains a fabric strip between the ends of the arch. This fabric strip may be medicated, a nonwoven fabric, cotton or other similar materials. The fabric strip may be used to dry between toes, apply medication to the area between toes, apply lotion or other similar actions.

DETAILED DESCRIPTION

As the population ages or increases in weight, issues with foot hygiene become apparent. Those who have had, for example, hip replacements, may not be able to bend sufficiently to perform simple activities such as drying between toes, applying lotions or medications or similar actions. Those with arthritic conditions may also have similar issues with regard to mobility. The overweight may find the action of bending to perform hygienic activities to toes and the space between toes difficult or impossible.

An embodiment of the arched holder may be made of any number of materials, however plastics and metal would be most useful. A fabric strip is attached between the ends of the arc of the arch. The handle of the device is sufficiently long such that it will be easily applied between the toes of the user without the user having to bend more than 90° at the waist, less than 75° and most preferably less than 55°.

The fabric strip is attached to the arched holder by clips. These may be friction clips similar to Velcro like materials that hold the fabric or simple clamps. In any event, the fabric strip is stretched across the arch with sufficient tension to prevent a deflection of the strip of no more than ⅓ of its length although other levels of deflection such as ¼, ⅛ and the like are inclusive in the invention.

The fabric strip may be cotton, a non-woven fabric or any other absorbent material that is capable of either drying between the toes or carrying a medication or lotion to the areas between the toes. Preferably the fabric strip would be disposable.

BRIEF DESCRIPTION OF THE DRAWING

FIG. 1, shows the foot-toe appendage hygiene device for drying, washing and application of medicament.

The device consists of a handle (1) and arch (2) as depicted in FIG. 1 and a fabric strip attached to the arch.

The Handle

The handle (1) of the arch is sufficiently long to allow for ease of use by those who have difficulty bending. In one embodiment, the handle is adjustable in length. In another embodiment the handle (1) is of fixed length. The handle (1) and the arch (2) are of any suitable material of construction, however plastic materials are highly preferred due to ease of cleaning and weight. Metal or wood may also be used to construct the handle (1) and arch (2). Particularly preferred materials for the handle (1) are polypropylene, polycarbonate, acrylonitrile-butadiene copolymers and the like. The arch may be attached to the handle via any suitable method or the entire handle (1) and arch (2) may be a single piece, for example injection molded plastics. Preferably, the handle (1) and the arch (2) are of the same material and may be cleaned or sterilized without causing damage to either item.

The Arch

The arch (2) has sufficient depth such that at its apex it will not prevent passage of the fabric strip between the toes. Thus, the arch (2) will have a depth of as high as 12 centimeters, 10 centimeters, 8 centimeters, 6 centimeters to as low as 3 centimeters as measured by drawing a straight line from the handle (1) portion to the end of the arch (2)—distance A as given in FIG. 1. The length of the arch is generally proportional to the depth, however an esthetically pleasing value may have the length of the arch approximately between 60 and 180 degrees of a circle, although a circular arch or ellipsoidal arch. An elliptical arch is equally acceptable and more esthetically pleasing as long as the depth of the arch is sufficient to allow smooth passage of the fabric strip between the toes.

The Fabric Strip

The fabric strip comprises a material such as cotton or a non-woven fabric. The fabric should be sufficiently absorbent to either dry between the toes or hold sufficient medication or lotion to allow application between the toes. The fabric strip may be disposable or reusable and must be of sufficient length to attach to the ends of the arch.

Attachment of the Fabric Strip

The fabric strip is attached between the ends of the arch by suitable means such as, but not limited to, clips, Velcro, spring loaded fasteners and similar devices. If the arch is plastic, these may be molded into the plastic item. The fastener needs to have sufficient clamping force such that the fabric strip ends are retained during the use of the device.

Use of the Device

The device would typically be used after other personal hygiene activities such as bathing. Drying between the toes prevents fungal infections and generally improves overall hygiene, extremely important to those with diabetes wherein many problems may arise with improper care of the feet that can result in loss of toes or the foot.

Application of medication between and upon the toes and foot may also be done using this device, again improving overall hygiene of the foot, particularly important for diabetics.

The invention claimed is:

1. A foot-toe appendage hygiene device for drying, washing and applying medicament comprising:
    an adjustable length linear handle;
    an elliptical arch element integral with said handle and extending from a distal end of said handle, wherein said arch element has a length proportional to a depth of said arch at an apex and two ends;
    an absorbent fabric strip extending between one of said two ends of said elliptical arch element and another of said two ends of said elliptical arch element;
    the absorbent fabric strip is detachably fastened to each of the two ends of said arch element by a fastener, wherein the each fastener is molded integrally with one of said two ends of the arch element and provides sufficient clamping force to retain said absorbent fabric strip element in an engaged position when the device is being used for drying, washing and applying medicament.

2. A foot-toe appendage hygiene device for drying, washing and applying medicament of claim 1 wherein the length of adjustable linear handle and elliptical arch enabling a user to bend at the waist no more than 90 degrees.

3. The foot-toe appendage hygiene device for drying, washing and applying medicament of claim 1 wherein the length of the adjustable linear handle and elliptical arch arrangement enabling a user not to bend at the waist more than 75 degrees.

4. The foot-toe appendage hygiene device for drying, washing and applying medicament of claim 1, wherein said elliptical arch has a depth between 3-12 centimeters.

5. The foot-toe appendage hygiene device for drying, washing and applying medicament of claim 1, wherein said absorbent fabric strip comprises a medicament or lotion.

6. The foot-toe appendage hygiene device for drying, washing and applying medicament of claim 1, wherein said absorbent fabric strip is disposable.

7. The foot-toe appendage hygiene device for drying, washing and applying medicament of claim 1, wherein said absorbent fabric strip is selected from the group consisting of cotton or non-woven fabrics.

8. The foot-toe appendage hygiene device for drying, washing and applying medicament of claim 1, wherein said integral linear handle and elliptical arch element is constructed from injected molded copolymers; wherein said copolymer is selected from the group consisting of polyethylene, polypropylene, polycarbonates and acrylonitrile-butadiene.

9. The foot-toe appendage hygiene device for drying, washing and applying medicament of claim 1, wherein said elliptical arch attachment elements are selected from the group consisting of clips and hook and loop fasteners.

* * * * *